United States Patent [19]

Hardy et al.

[11] Patent Number: 5,097,057

[45] Date of Patent: * Mar. 17, 1992

[54] PHOSPHATE AND PHOSPHONATE COMPOUNDS INCLUDING AND DERIVED FROM PHOSPHATE AND/OR PHOSPHONATE-CONTAINING HYDROGEN PHOSPHONATES

[75] Inventors: Thomas A. Hardy, Thousand Oaks, Calif.; Edward N. Walsh, New City, N.Y.

[73] Assignee: Akzo America Inc., Dobbs Ferry, N.Y.

[*] Notice: The portion of the term of this patent subsequent to Feb. 28, 2006 has been disclaimed.

[21] Appl. No.: 414,781

[22] Filed: Sep. 29, 1989

Related U.S. Application Data

[60] Continuation of Ser. No. 258,536, Oct. 17, 1988, Pat. No. 4,883,891, which is a division of Ser. No. 20,829, Mar. 2, 1987, Pat. No. 4,808,744, which is a continuation of Ser. No. 737,128, May 23, 1985, abandoned.

[51] Int. Cl.⁵ .............................................. C07F 9/40
[52] U.S. Cl. ..................................... 558/163; 558/161
[58] Field of Search ................................. 558/161, 163

[56] References Cited

U.S. PATENT DOCUMENTS 3,332,893  7/1967  Birum et al. ......................... 558/84
3,391,226  7/1968  Birum et al. ......................... 558/163
4,808,744  2/1989  Hardy et al. ........................ 558/163
4,883,891  11/1989  Hardy et al. ........................ 558/161
4,886,895  12/1989  Hardy et al. ........................ 558/161

OTHER PUBLICATIONS

Arbuzov et al, Journal of General Chemistry of USSR, 29 p. 2582 (1959) (English Translation).
Abrurzov et al. Chemical Abstracts, vol. 54, No. 10836 (1960).

*Primary Examiner*—Mukund J. Shah
*Assistant Examiner*—E. Bernhardt
*Attorney, Agent, or Firm*—Richard P. Fennelly; Louis A. Morris

[57] ABSTRACT

There are disclosed novel phosphorus-containing compounds including and derived from hydrogen phosphonates. The compounds of the present invention can be prepared by reacting a hydrogen phosphonate with: (a) an ethylene derivative in a Michael reaction, (b) an amine or amide and formaldehyde in a Mannich reaction, (c) an aldehyde or ketone, (d) a halogen, (e) carbon tetrachloride and an alkylamine, and (f) carbon tetrachloride and a hydroxyphosphonate. Halophosphonates produced according to procedure (d) can also be used in reactions with (a) alkylamines and (b) hydroxyphosphonates or epoxides to produce the compounds of the present invention.

2 Claims, No Drawings

PHOSPHATE AND PHOSPHONATE COMPOUNDS INCLUDING AND DERIVED FROM PHOSPHATE AND/OR PHOSPHONATE-CONTAINING HYDROGEN PHOSPHONATES

This application is a continuation of U.S. Ser. No. 258,536, filed Oct. 17, 1988 now U.S. Pat. No. 4,883,891, which is a divisional of U.S. Ser. No. 020,829, filed Mar. 2, 1987, now U.S. Pat. No. 4,808,744, which, in turn, is a continuation of U.S. Ser. No. 737,128, filed May 23, 1985, now abandoned.

FIELD OF THE INVENTION

The present invention relates to a novel class of phosphate and phosphonate compounds including and derived from a phosphate-containing or phosphonate-containing hydrogen phosphonate.

BACKGROUND OF THE INVENTION

In today's modern technology, phosphorus compounds play an increasingly important role. These compounds find utility as flame retardant additives for plastics and textiles, lubricant additives, biocides, herbicides, insecticides, pesticides, fungicides, growth regulators, ore flotation agents and metal plating additives.

Various classes of phosphorus derivative compounds are known.

U.S. Pat. No. 3,042,701 discloses phosphorus compounds having a plurality of pentavalent phosphorus ester radicals. The compounds disclosed in the above patent are selected from the class consisting of phosphate diesters and phosphate-containing polyesters. The pentavalent state is achieved by the oxidation or thionation of the phosphite-phosphonate intermediates to phosphate-phosphonates.

U.S. Pat. No. 2,372,244 discloses a process for the preparation of what the inventors believe to be "analogs of the alkylene glycol substituted partial esters of the acids of phosphorus".

U.S. Pat. No. 3,525,705 discloses a method for the production of fire resistant polyurethane products. In the method disclosed in the above patent, an organic polyisocyanate is reacted with the reaction product of the monoester of phosphoric acid, a mono or diester of diphosphoric acid, or a mono or diester of pyrophosphoric acid and an epoxide.

U.S. Pat. No. 2,909,559 discloses a process for producing hydroxyl-containing polymeric phosphate esters by heating a hydroxyl-containing phosphate ester of the structure:

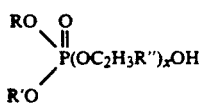

to a temperature of from about 90° C. to about 250° C.

SUMMARY OF THE INVENTION

The present invention is directed to compounds having the formula:

$$(RO)_n(R_1O)_{2-n}P(O)Z$$

wherein

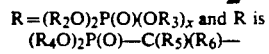

and R is

$R_1$, $R_2$ and $R_4$ are the same or different and are alkyl, haloalkyl, aryl or haloaryl groups of from 1 to about 20 carbon atoms, $R_5$ and $R_6$ are the same or different and are hydrogen, alkyl, haloalkyl, aryl or haloaryl groups of from 1 to about 20 carbon atoms, $R_3$ is alkylene or haloalkylene of from 2 to about 10 carbon atoms, n is an integer from 1 to 2, x is an integer from 1 to 10, Z is hydrogen or a number of other substituents to be defined below. Preferably, the alkyl, haloalkyl, aryl and haloaryl groups contain from 1 to about 20 carbon atoms and the alkylene and haloalkylene groups contain from about 2 to about 10 carbon atoms. As used herein, the designation "P(O)" is meant to be synonymous to the moiety P=O.

The present invention is also directed to a number of methods for the synthesis of the compounds of the present invention. Although a variety of methods are used to synthesize the compounds of the present invention, the starting material is a hydrogen phosphonate of the formula $(RO)_n(R_1O)_{2-n}P(O)$—Z wherein R, $R_1$ and n are as previously defined and Z is hydrogen.

The hydrogen phosphonate used as a starting material for the novel compounds of the present invention is synthesized by reacting an alcohol of the formula ROH wherein R is as previously defined with a dialkyl phosphite of the formula $(R_1O)_2P(O)H$ wherein $R_1$ is as previously defined. The hydrogen phosphonate thus synthesized is then used in a variety of reactions wherein Z is derived from a number of sources. Alternatively, a halophosphonate may also be used.

In an embodiment of the present invention, Z is derived from the reaction of a hydrogen phosphonate with an ethylene derivative in a Michael addition reaction.

In one other embodiment, Z is derived from a Mannich reaction in which a hydrogen phosphonate of the present invention is treated with an amine or amide and formaldehyde to yield the desired product.

In another embodiment, Z is derived from the reaction of a hydrogen phosphonate of the present invention with an aldehyde or ketone to yield the desired product.

In yet another embodiment, a hydrogen phosphonate of the present invention is reacted with a halogen to yield a halophosphonate. The halo phosphonate, itself a compound of the present invention, can also be used as a starting material for reactions in which Z is derived from a variety of sources.

In still another embodiment, Z is an amide group derived from the reaction of a hydrogen phosphonate of the present invention with carbon tetrachloride and an alkylamine. Alternatively, a halophosphonate produced as previously described is reacted with an alkylamine to yield the desired product.

Another method by which the compounds of the present invention may be produced involves the reaction of a halo phosphonate of the present invention with either a phosphate-containing or phosphonate-containing alkoxy or phenoxy group or an oxirane derivative to yield a product wherein Z is said alkoxy or phenoxy group. Alternatively, a hydrogen phosphonate of the present invention is reacted with carbon tetrachloride and a phosphonate-containing or phosphate-containing alkoxy or phenoxy group to yield a product wherein Z is said alkoxy or phenoxy group.

Further features of the present invention can be seen in the Detailed Description of the Invention which follows.

DETAILED DESCRIPTION OF THE INVENTION

The present invention is directed to novel phosphorus containing compounds of the formula:

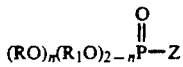

wherein

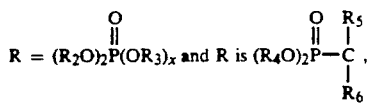

$R_1$, $R_2$, and $R_4$ are the same or different and are alkyl, haloalkyl, aryl, or haloaryl, $R_5$ and $R_6$ are the same or different and are hydrogen, alkyl, haloalkyl, aryl, or haloaryl, $R_3$ is alkylene or haloalkylene, n is 1 or 2, x is an integer from 1 to 10, Z is hydrogen or a number of substituents to be described in detail hereinafter. Preferably, the alkyl, haloalkyl, aryl and haloaryl groups contain from 1 to about 20 carbon atoms and the alkylene and haloalkylene groups contain from 2 to about 10 carbon atoms.

The compounds of the present invention may be produced by a number of processes.

The starting material for the synthesis of the compounds of the present invention is a hydrogen phosphonate of the formula $(RO)_n(R_1O)_{2-n}P(O)H$ wherein R, $R_1$, and n are as previously defined. One such method for the synthesis of a hydrogen phosphonate is disclosed in the co-pending application of E. N. Walsh and T. A. Hardy entitled "Phosphate and Phosphonate-containing Phosphate Esters, now U.S. Pat. No. 4,697,030, the subject matter therein being incorporated herein by reference. The method disclosed in the aforementioned application involves the transesterification of an alcohol represented by the formula ROH wherein R is as defined previously with a dialkyl phosphite of the formula $(R_1O)_2P(O)H$ wherein $R_1$ is as defined previously, according to the following general reaction:

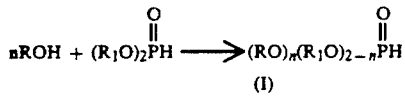

compounds of Formula I, hydrogen phosphonates, are then used as starting materials for the synthesis of the compounds of the present invention.

In one embodiment, Z is derived from a Michael reaction between the hydrogen phosphonate and a ethylene derivative. The Michael reaction is a well known reaction, a complete description of which can be found in *The Merck Index*, Tenth Edition, 1983 "Organic Name Reactions" ONR-60. This reaction involves the base catalyzed addition of carbanions to activated unsaturated systems. By definition a carbanion is an anion in which carbon carries a negative charge, see Morrison and Boyd, *Organic Chemistry*, Fourth Edition, p. 859. In the present invention, a hydrogen phosphonate is reacted with an alkylene derivative as follows:

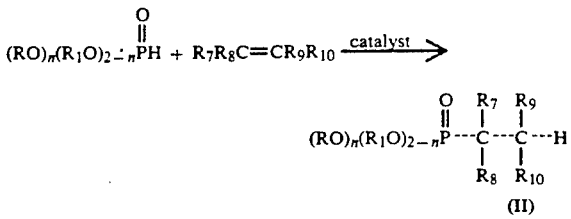

wherein R, $R_1$ and n are as previously defined. $R_7$, $R_8$, $R_9$ and $R_{10}$ may be the same or different and are hydrogen, alkyl, halogen, haloalkyl, acyl, or

wherein R' and R" are the same or different and are alkyl, aryl, heterocyclic or substituted alkyl, aryl or heterocyclic, amide, haloacyl, or cyano.

Non-limiting examples of alkylene derivatives which may be used in a Michael reaction are:
CH$_2$=CHCO$_2$H
CH$_2$=CCH$_3$CO$_2$CH$_3$
CH$_2$=CH—C≡N
CH$_2$=CH—CONH$_2$
CH$_2$=CH—CHO Examples of suitable catalysts which may be used in the above Michael reaction include sodium methoxide, sodium ethoxide, potassium methoxide or potassium ethoxide.

In another embodiment, Z is derived from a Mannich reaction in which a hydrogen phosphonate of the present invention is reacted with an amine or amide and formaldehyde. The Mannich reaction involves the reaction of an active methylene compound with formaldehyde and ammonia or primary or secondary amines to give beta-aminocarbonyl compounds. This reaction is fully described in *The Merck Index*, Tenth Edition p. ONR-57. In the present invention, a hydrogen phosphonate is treated with an amine or amide and formaldehyde according to the following general reaction,

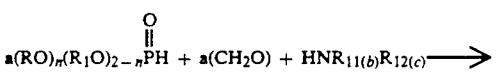

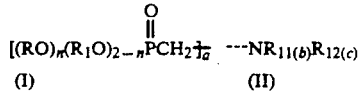

wherein R, $R_1$ and n are as previously defined, $R_{11}$ and $R_{12}$ may be the same or different and are hydrogen, alkyl, haloalkyl, hydroxyalkyl or acyl, a is an integer from 1 to 3, b and c may be zero or an integer from 1 to 2 with the restriction that a+b+c=3.

Examples of amines or amides which may be used in a Mannich type reaction are
NH$_3$
CH$_3$NH$_2$
CH$_3$NHCH$_3$
CH$_3$CH$_2$NH$_2$
C$_6$H$_5$—NH—C$_6$H$_5$
HOCH$_2$CH$_2$NH$_2$
(HOCH$_2$CH$_2$)$_2$NH In another embodiment of the present invention, Z is derived from the reaction of a hydrogen phosphonate of the present invention with an aldehyde or ketone according to the following general reaction.

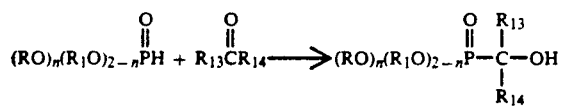

wherein R, $R_1$ and n are as previously defined and $R_{13}$ and $R_{14}$ are the same or different and are hydrogen, alkyl, haloalkyl, aryl, or haloaryl.

The reaction of the hydrogen phosphonate with the aldehyde or ketone takes place in the presence of a catalyst such as triethylamine.

Examples of suitable aldehydes and ketones which can be used in a reaction where a hydrogen phosphonate is reacted with an aldehyde or ketone (C(O)=C=O) include:

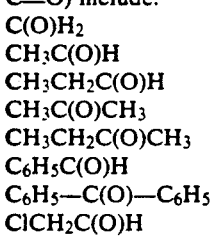

In another embodiment of the present invention, Z may be a halogen. In addition to the formation of a compound of the present invention, this reaction is also extremely important since the halo phosphonates formed are also intermediates useful in the synthesis of other compounds of the present invention. The reaction proceeds as follows:

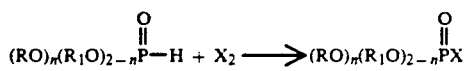

wherein R, $R_1$ and n are as defined previously and X is a halogen, i.e., fluorine, chlorine, bromine or iodine.

In a further embodiment of the present invention, Z is an amide group. A phosphoramidate of the present invention can be prepared by either of two methods. In the first method, a halo phosphonate prepared according to the previously described method is reacted with an alkylamine, in either the mono-, or disubstituted form:

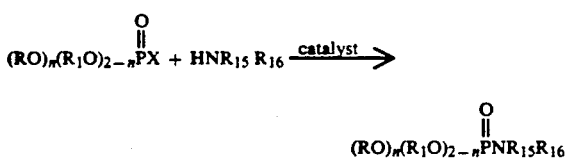

wherein R, $R_1$, n and X are as previously defined and $R_{15}$ and $R_{16}$ are the same or different and are hydrogen, alkyl, haloalkyl and hydroxyalkyl.

In an alternative method, a hydrogen phosphonate of the present invention is reacted with carbon tetrachloride followed by reaction with an alkylamine in a reaction as follows:

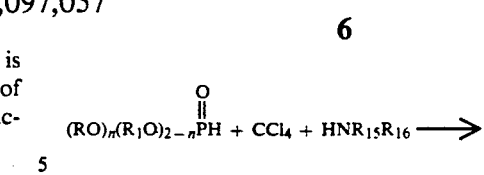

wherein R, $R_1$, n, $R_{15}$ and $R_{16}$ are as previously defined.

Illustrative amines which may be used in the above synthesis routes include:
$NH_3$
$CH_3NH_3$
$(CH_3)_2NH$
$C_6H_5-NH-C_6H_5$
$HOCH_2CH_2NH_2$
$(HOCH_2CH_2)_2NH$ In yet another embodiment of the present invention, Z is an alkoxy or phenoxy group. A phosphate ester of this invention may be prepared by a number of methods.

In one method, a halo phosphonate is reacted with an alcohol according to the following reaction:

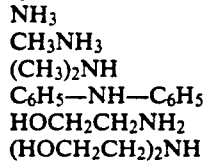

wherein R, $R_1$, n and x are as previously defined and $R_{17}$ may be alkyl, haloalkyl, aryl, haloaryl, hydroxyalkyl or $R_{17}$ may be the same as R.

In an alternative method a hydrogen phosphonate is reacted with carbon tetrachloride and an alcohol in the presence of a base, or a phosphate-containing or phosphonate-containing alkoxy or phenoxy group according to the reaction:

wherein R, $R_1$, n and $R_{17}$ are as previously defined.

In yet another method, a halo phosphonate is reacted with an epoxide:

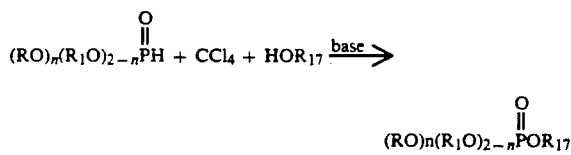

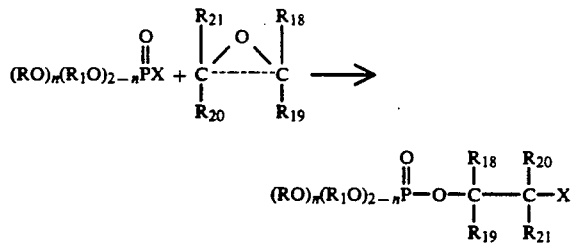

wherein R, $R_1$, n and X are as defined previously and $R_{18}$, $R_{19}$, $R_{20}$ and $R_{21}$ are the same or different and are hydrogen, alkyl and haloalkyl.

Non-limiting examples of suitable alcohols represented by the formula $R_{17}OH$ include:
$CH_3OH$
$CH_2CH_2OH$
$ClCH_3CH_2OH$
$CH_2BrCHBrCH_2OH$
$C_6H_5OH$ CH₃(CH₂)₇OH
(CH₃CH₂O)P(O)CH₂OH
(CHBrCHBrCH₂O)₂P(O)OCH₂CH₂OH Non-limiting examples of epoxides represented by the formula:

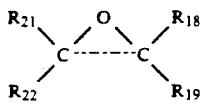

include:

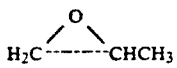

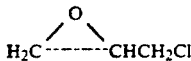

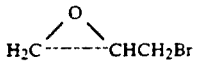

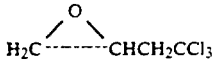

The present invention is further illustrated by the following examples and procedures.

EXAMPLE 1

Preparation of Diethyl Hydroxymethylphosphonate

To a 2 liter, round bottomed flask fitted with a nitrogen inlet were added 500 grams (3.6 mole) of diethyl phosphite (Aldrich), 120 grams (3.8 mole) of paraformaldehyde (Baker) and approximately 6 milliliters of triethylamine. The mixture was stirred overnight at room temperature but no visible reaction had occurred so approximately 10 milliliters more of triethylamine was added and the mixture was slowly warmed to 90° C. The solution was heated for approximately an additional hour, filtered hot and distilled. 320 grams of a liquid product corresponding to a 60% yield was obtained.

EXAMPLE 2

This Example shows the transesterification of diethyl hydroxymethylphosphonate with diethyl phosphite.

To a 1 liter round bottomed flask equipped with a Vigreaux column, distillation head and dry ice receiver were added 140 grams of diethylhydroxymethyl phosphonate synthesized by the procedure of Example 1, 70 grams of diethyl phosphite and 2.0 grams of sodium ethoxide. The pressure was reduced to ~25 mm. Hg with an aspirator and the solution was heated to 95° C. to about 105° C. 0.8 grams of sodium ethoxide was then added and the solution was heated at 115° C. and 25 mm Hg for 6 hours. The acid number of the compound at this point was 14.6.

In order to obtain a pure preparation, i.e. 3 P/mole, 30 grams (0.18 mole) of diethylhydroxymethylphosphonate (acid number=4.6) was added and the reaction mixture was heated to 115° at 25 mm Hg with a dry ice receiver. 6.6 grams of a product having an acid number of 15.4 was obtained.

EXAMPLE 3

This Example illustrates the reaction of a diphosphonophosphite with an aldehyde.

To a flask containing 116 grams (0.304 mole) of the diphosphonophosphite synthesized by the procedure of Example 2 were added 6.0 grams (0.036 mole) of triethyl phosphite (STAUFFER) and 5 grams of triethylamine (Aldrich). The mixture was placed under nitrogen and slowly warmed to 65° C. The mixture was cooled and 11 grams of paraformaldehyde was added over a 5 minute period. The reaction mixture was then heated to ~65° C. for three hours.

The reaction mixture was then stripped on wipe film at 110°-115° C. at 1 mm Hg. Analytical data showed
methanol/acid # = 3.4 mg KOH/g
H₂O/acid # = 10.1 mg KOH/g To determine the HCl acid number, 2.0 grams of the sample were added to 11.3 grams of 0.1 HCl and the solution was stirred for 10 minutes. Titration to the methyl red end point (pH 4.5) required 15.3 milliliters of 0.1N KOH. After correction for HCl, acid number=11.7. Titration to the phenolphthalein end point (pH 9-10) required 55 milliliters KOH (after correction, acid number=130).

The compound had the formula:

EXAMPLE 4

Similar to Example 3 except sodium methoxide was used as a catalyst. 360 grams of product was obtained.

Procedure 1

By reacting a hydrogen phosphonate of the present invention with an amine or amide and formaldehyde and following the procedure of the Mannich reaction, a compound where Z is an amine or amide is obtained.

Procedure 2

By reacting a hydrogen phosphonate of the present invention with a halogen under known conditions for halogenation of phosphonate compounds, a halo phosphonate is obtained.

Procedure 3

By reacting a hydrogen phosphonate of the present invention or a halo phosphonate produced by the method of Procedure 2 with an alkylamine, or an alkylamine plus carbon tetrachloride if a hydrogen phosphonate is the starting material, a compound in which Z is an amide group is obtained.

Procedure 4

By reacting the hydrogen phosphonate produced in Example 2 with an alcohol in the presence of carbon tetrachloride, a compound wherein Z is an alkoxy or phenoxy group is obtained. For instance, if a hydrogen phosphonate is reacted with ethanol, the compound produced would have the formula:

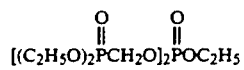

Alternatively, by reacting a halo phosphonate produced in Procedure 2 with a hydroxyphosphonate or an oxirane, a compound in which Z is an alkoxy or phenoxy group is obtained.

Procedure 5

By reacting an alpha, beta unsaturated carbonyl compound with a hydrogen phosphonate of the present invention and following the procedures of the Michael addition reaction, a compound in which Z is an alkylene derivative is obtained.

An especially suitable use of a compound of the present invention would be as flame retardants according to the following procedures.

Procedure 6

By combining a suitable amount of a compound of the present invention with a long chain polyol such as pentaerythritol or dipentaerythritol and a nitrogenous compound such as melamine, a char forming flame retardant additive capable of being incorporated into thermoplastic resins is obtained. Well known procedures for the formation of these additives can be used and the amount of flame retardant to be incorporated to give a V-O rating in the well known UL-94 test can be determined by procedures well known to those skilled in the art.

Similarly, a compound of the present invention can be included in a flexible or rigid polyurethane foam formulation so as to produce a foam product having flame retardant properties.

Additional features of the preferred and most preferred embodiments of the present invention can be found in the claims hereinafter.

What is claimed is:

1. A compound of the formula:

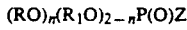

wherein R is

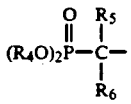

$R_1$ and $R_4$ are the same or different and are alkyl, aryl or haloaryl, $R_5$ and $R_6$ are the same or different and are alkyl, haloalkyl, aryl, or haloaryl, n is 2, and Z is

with $R_{13}$ and $R_{14}$ being the same or different and are hydrogen, alkyl, haloalkyl, aryl, or haloaryl.

2. A compound as claimed in claim 1 wherein $R_4$ is ethyl.